(12) United States Patent
Lofthouse et al.

(10) Patent No.: US 11,007,360 B2
(45) Date of Patent: May 18, 2021

(54) MULTI-PURPOSE CAP FOR FLUID PORTS ON A MEDICAL DEVICE

(71) Applicant: Fresenius Medical Care Holdings, Inc., Waltham, MA (US)

(72) Inventors: Nicholas Garrett Lofthouse, Roy, UT (US); Devon Bradly Hall, Syracuse, UT (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 0 days.

(21) Appl. No.: 16/980,883

(22) PCT Filed: Mar. 5, 2019

(86) PCT No.: PCT/US2019/020631
§ 371 (c)(1),
(2) Date: Sep. 15, 2020

(87) PCT Pub. No.: WO2019/212637
PCT Pub. Date: Nov. 7, 2019

(65) Prior Publication Data
US 2021/0038878 A1    Feb. 11, 2021

Related U.S. Application Data

(60) Provisional application No. 62/664,993, filed on May 1, 2018.

(51) Int. Cl.
| A61M 39/20 | (2006.01) |
| A61M 1/36 | (2006.01) |
| A61M 1/14 | (2006.01) |

(52) U.S. Cl.
CPC .............. *A61M 39/20* (2013.01); *A61M 1/14* (2013.01); *A61M 1/367* (2013.01)

(58) Field of Classification Search
CPC .. A61M 39/20; A61M 2039/205; A61M 1/14; A61M 1/1621; A61M 1/367; A61J 1/1475; A61J 1/1481; A61J 1/1487; A61J 1/2048; A61J 1/2058
See application file for complete search history.

(56) References Cited

U.S. PATENT DOCUMENTS

| 3,691,068 | A | | 9/1972 | Cross |
| 4,324,662 | A | | 4/1982 | Schnell |
| 5,536,412 | A | | 7/1996 | Ash |
| 5,858,238 | A | | 1/1999 | McRea et al. |
| 5,954,957 | A | * | 9/1999 | Chin-Loy ............. A61M 39/20 210/232 |
| 6,830,685 | B2 | | 12/2004 | Pope et al. |

(Continued)

OTHER PUBLICATIONS

International Search Report and Written Opinion issued in corresponding International Patent Application No. PCT/US2019/020631 dated May 31, 2019 (12 pages).

*Primary Examiner* — Philip R Wiest
(74) *Attorney, Agent, or Firm* — Kilyk & Bowersox, P.L.L.C.

(57) ABSTRACT

A multi-purpose cap adapted to fit onto fluid ports of different sizes and configurations of medical devices used for purifying or concentrating biological samples, wherein the cap is adapted to press fit onto diverse fluid ports on dialyzers and other blood treatment devices.

37 Claims, 7 Drawing Sheets

(56) References Cited

U.S. PATENT DOCUMENTS

| | | |
|---|---|---|
| 7,063,816 B2 | 6/2006 | Maianti et al. |
| D883,476 S | 5/2020 | Lofthouse et al. |
| 2014/0263018 A1 | 9/2014 | Fuhriman |

* cited by examiner

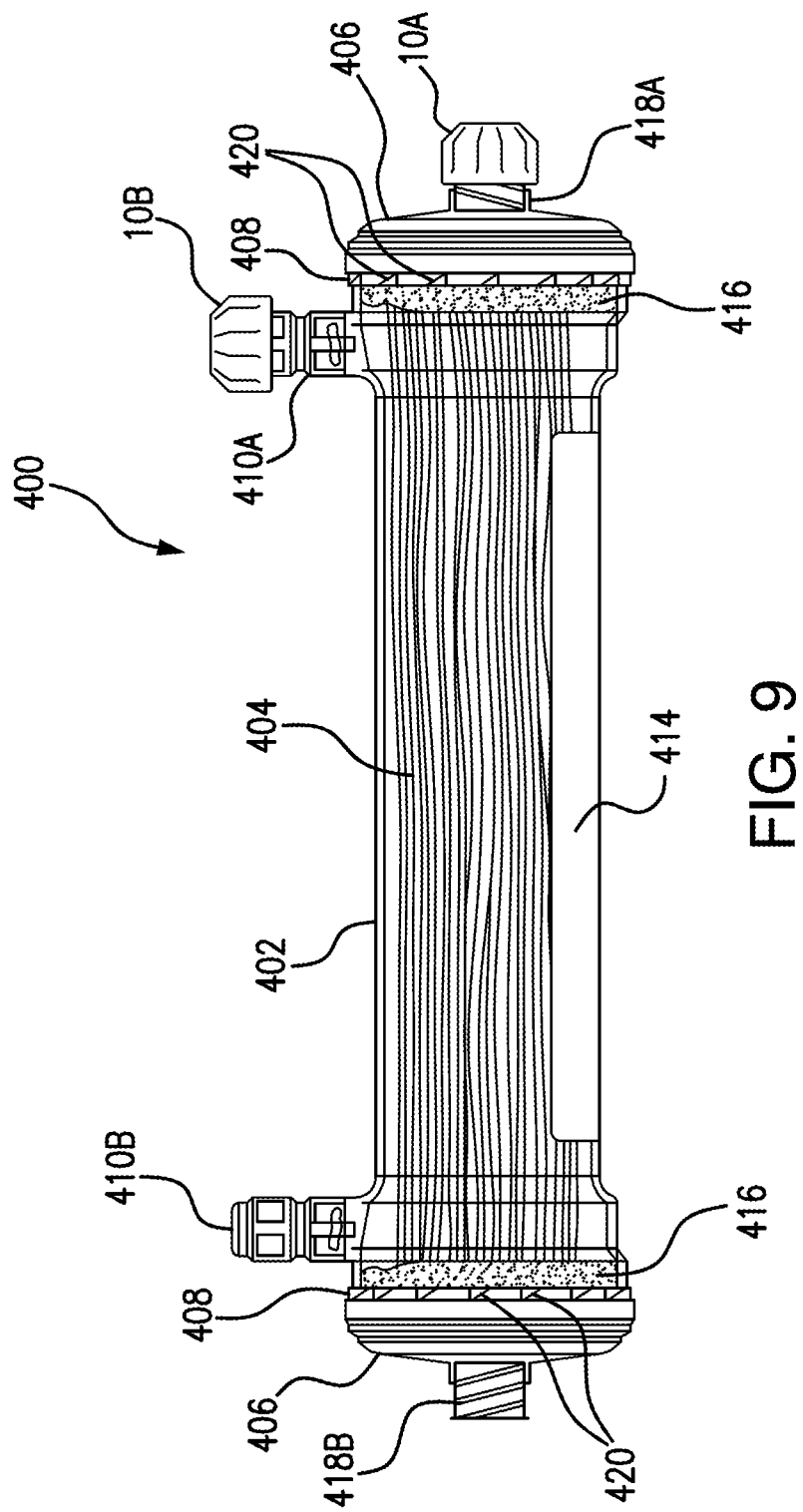

MULTI-PURPOSE CAP FOR FLUID PORTS ON A MEDICAL DEVICE

This application is a National Stage Application of PCT/US2019/020631, filed Mar. 5, 2019 which claims the benefit under 35 U.S.C. § 119(e) of prior U.S. Provisional Patent Application No. 62/664,993, filed May 1, 2018, which is incorporated in its entirety by reference herein.

FIELD OF THE INVENTION

The present invention relates to a multi-purpose cap adapted to fit onto fluid ports of different sizes and configurations of medical devices used for purifying or concentrating biological samples, and particularly relates to a closure cap adapted to press fit onto diverse fluid ports on dialyzers and other blood treatment devices.

BACKGROUND OF THE INVENTION

Medical devices used for the treatment of biological liquids such as blood commonly have a semipermeable membrane structure contained inside a housing. Normally, the biological liquid to be treated is passed into the housing so as to contact one side of the membrane, and, depending on the function of the device, the other side of the membrane may be simultaneously contacted by another liquid passed into the housing. The membrane effects selective transfer of certain liquids and solutes from one liquid to the other liquid or membrane side through the membrane. Medical devices of these types include, for example, dialyzers, hemofilters, hemodiafilters, and hemoconcentrators. These medical devices may be used in extracorporeal blood treatment systems or other types of biological liquid treatment systems.

Fluid ports are required in order to effect introduction and discharge of liquids into and out of such medical devices. A dialyzer, for example, is a filter device which can be used by patients with kidney failure who suffer from the adverse effects of waste and fluid build-up in their blood that are normally eliminated by the kidneys. A conventional dialyzer, such as a hemodialysis dialyzer, has blood ports and dialysate ports. The blood ports are used for introduction and discharge of blood flow from the dialyzer device during a dialysis treatment. Blood can be passed through the membrane structure, such as hollow fiber bundles or other membranes, arranged within a hollow cylindrical-shaped tube portion of the dialyzer between the blood introduction and discharge ports. The dialysate ports are used for introduction and discharge of dialysate fluid to and from the same device. Dialyzers and components thereof of these types are shown, for example, in U.S. Pat. Nos. 3,691,068, 4,324,662, and 6,830,685, all of which are incorporated in their entireties by reference herein. In dialyzer arrangements such as shown in these patents, the blood ports are located at opposite ends of the tube portion, and ports used for the dialysate fluid are arranged to extend from the sidewall of the tube portion near the opposite ends of the device.

Hemafilters have been used, among other things, to filter molecules of molecular weights associated with toxins across a membrane for removal of the toxins from blood. Hemafilters can also have a bundle of hollow fibers or other membrane structure encapsulated in a housing, wherein passage of another fluid through the device is provided on the opposite side of the membrane from blood side, so the devices typically include introduction and discharge ports for each side of the membrane. Examples of hemafilters are shown in U.S. Pat. No. 5,536,412, which is incorporated in its entirety by reference herein. Hemoconcentrators have been used as an ultrafiltration system to remove excess fluid from blood as part of cardiopulmonary bypass procedures. A hemoconcentrator can also have a bundle of hollow fibers or other membrane structure encapsulated in a housing which has blood ports at opposite ends of the device, and includes at least one additional device port for discharge of ultrafiltered fluid collected on the opposite side of the membrane in the device. A vacuum line may be coupled to the discharge port(s) to assist removal of the ultrafiltered fluid from the device. Examples of hemoconcentrators are shown in U.S. Pat. Nos. 5,858,238 and 7,063,816, which are incorporated in their entireties by reference herein.

The blood ports and the dialysate ports or other kinds of ports on such blood treatment devices generally have male configurations extending from the device housing or ends thereof. For safety, e.g., to prevent accidental misconnections, blood ports typically have different geometrical profiles from the dialysate ports or other kinds of ports on the same blood treatment devices.

After their manufacture, dialyzers typically are sterilized. Sterilization of these devices by steam, irradiation or chemicals can be used. The blood side in particular of the dialyzer needs to be kept sterile until the device is used. Removable disposable closure caps have been used to cover the blood ports of the sterilized dialyzers. Further, a used dialyzer can contain residual fluid, and closure caps can be used to cover blood ports, dialyzer ports, or both of a used dialyzer for disposal safety, such as disclosed in U.S. Patent Application Publ. No. 2014/0263018 A1, which is incorporated in its entirety by reference herein.

Contemporary caps for blood treatment devices are typically made of a molded plastic material suitable for medical applications, but typically are designed to cover only one type of port, e.g., either a blood port or a dialysate port of a dialyzer. A multi-purpose cap for hydraulic ports on a medical device is shown in U.S. Pat. No. 5,954,957, wherein the cap includes external lugs used to thread into a female threaded collar of a DIN blood port using manual twisting.

There is a need for a medical device cap capable of fitting on ports of different geometries on the same dialyzer or other blood treatment device, which can be readily and securely press fit onto any of the different device ports on the same device to provide a sealed closure of any of the ports.

SUMMARY OF THE INVENTION

A feature of the present invention is a multi-purpose closure cap adapted to press fit onto fluid ports of different sizes and configurations on medical devices used in medical applications.

A further feature of the present invention is a multi-purpose closure cap which can be press fit onto each of a blood port and a separate dialysate port of a blood treatment device.

Another feature of the present invention is a blood treatment device which includes such a press fitting port cap.

An additional feature of the present invention is a dialyzer which includes at least one of such port caps press fit onto one or more of the blood ports, dialysate ports, or both, of the dialyzer.

To achieve these and other advantages and in accordance with the purposes of the present invention, as embodied and broadly described herein, the present invention relates, in part, to a closure cap for fluid ports on a blood treatment device, comprising a first skirt, a second skirt located radially within the first skirt, wherein the first skirt and the second skirt are separated by an intermediate channel, and a transverse connecting portion which connects the first skirt and the second skirt, which comprises an outer surface, wherein the first skirt comprises a first skirt upper portion and a first skirt lower portion, wherein the first skirt upper portion extends away from the transverse connecting portion, and a circumferential inner side surface of the first skirt upper portion is configured to sealingly engage an upper external surface of a first fluid port on a blood treatment device, and the first skirt lower portion comprises a cylindrical sleeve portion and a plurality of ribs extending inward from the cylindrical sleeve portion, wherein the ribs are spaced apart around an inner side surface of the cylindrical sleeve portion and are configured to engage an external shroud surrounding a second fluid port on the blood treatment device; and the second skirt comprises a second skirt upper portion and a second skirt lower portion, wherein the second skirt upper portion extends away from the transverse connecting portion and comprises an exposed bottom stop surface and a circumferential external side surface that is surrounded by the channel, wherein the circumferential external side surface of the second skirt upper portion is configured to sealingly engage with an upper internal surface of the first fluid port, and the second skirt lower portion comprises a tubular skirt which extends away from the second skirt upper portion, wherein the tubular skirt is externally surrounded by the channel and comprises a circumferential internal side surface configured to sealingly engage with an external surface of the second fluid port, wherein the second fluid port has a smaller external diameter from that of the first fluid port, and wherein the exposed bottom stop surface of the second skirt upper portion provides a hard stop to pushing of the tubular skirt onto the second fluid port of the blood treatment device.

The present invention further relates to a blood treatment device comprising at least one first fluid port having a first external diameter and at least one second fluid port having a second external diameter, wherein the second external diameter is smaller than the first external diameter, and at least one of the at least one first fluid port, the at least one second fluid port, or both, are each closed with the closure cap.

The present invention further relates to a dialyzer with the closure cap used as a dialyzer port cap.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. Similar referencing identifiers in different figures can refer to similar features unless indicated otherwise.

BRIEF DESCRIPTION OF THE DRAWINGS

FIG. 9 shows a dialyzer which has closure caps fitted onto blood and dialysate ports according to an example of the present application.

DETAILED DESCRIPTION OF THE INVENTION

Figure 1:
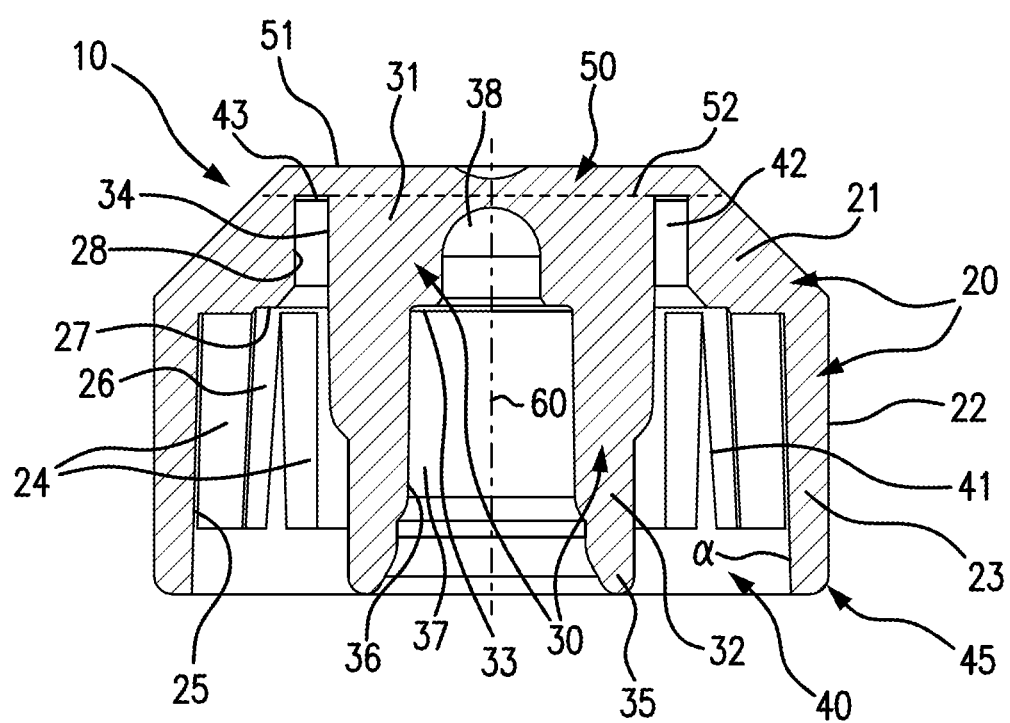
FIG. 1 shows a cross-sectional view of a closure cap according to an example of the present application.

The present invention relates to a multi-purpose cap which is adapted to press fit on, and thus cover, any of several different types of male fluid connection ports provided on blood treatment devices, such as hemodialyzers, hemofilters, hemodiafilters, and hemoconcentrators. The blood treatment device which can have ports closed with caps of the present invention can have multiple blood ports (e.g., one for fluid input and another for fluid output) for the one side of the membrane, and at least one differently dimensioned dialysate port for the other side of the membrane, e.g., two dialysate ports (one for fluid input and another for fluid output) or a dialysate port for removal of ultrafiltered fluid. As indicated, the blood ports are typically dimensioned differently from the dialysate port(s) on the blood treatment devices to prevent accidental misconnection. As used herein, "blood" ports are used for introducing into and removing from the blood treatment device the biological fluid (such as extracorporeal blood) to be treated by the device. The "dialysate" ports are used for introducing into and removing from the blood treatment device a liquid used for treating the biological fluid in the device, or for only removing an ultrafiltered liquid from the blood treatment device. For a hemodialyzer, for example, one blood port on a dialyzer can be used for arterial blood input and another for venous blood output for the blood side of the membrane, and differently dimensioned dialysate ports can be used for the other side of the membrane with one dialysate port used for fresh or regenerated dialysate liquid input and another for spent dialysate liquid output.

When fully attached to one of the indicated medical device fluid ports so as to sealingly close the port, the cap can serve to maintain an internal condition (such as sterility or cleanliness) of an unused blood treatment device until time of use. If used to close a port on a used blood treatment device for disposal, the cap can serve to keep residual process fluids within the device.

The blood ports and dialysate ports of blood treatment devices which can be capped using a cap of the present invention can be dimensioned according to internationally recognized standards. The cap can be used and seals on both ISO compliant ports (i.e., the blood port and the dialysate port) of a dialyzer or other blood treatment device having ISO-compliant ports. As an option, the cap of the present invention can be fitted onto blood ports and dialysate ports of blood treatment devices wherein the ports are configured according to DIN EN ISO 8637 (e.g., ISO 8637-2:2017), which standards are incorporated herein by reference. As used herein: a "DIN blood port" has a male nipple with a surrounding female threaded shroud or collar as defined by DIN EN ISO 8637 (e.g., ISO 8637-2:2017), and a "DIN dialysate port" has a profile as defined in the same standard(s).

The cap of the present invention can be press fit on any of these different types of ports on a blood treatment device. The cap of the present invention therefore can unify a blood port cap and a dialysate cap combining both functions into a single working cap. This can reduce manufacturing costs and simplify use of the blood treatment device since only a single type of cap needs to be provided per blood treatment device. This avoids the need to include separately designed and manufactured dialysate port caps (which also can be referred to as adapter caps) from blood port caps, in packaging in which a dialyzer or blood treatment device is supplied to a user. This can allow cost savings by eliminating the need for separate dialysate caps (two out of four caps) from the dialyzer packages sent to hemodialysis clinics. Dialyzers or other blood treatment devices can be delivered to hemodialysis clinics or other users with the blood port caps connected to preserve sterility of the device during pre-use handling and storage, and without needing to include different caps on the dialysate ports or loosely within the packaging, which possibly could fall on the floor when a clinician opens the package, rendering them unusable. A pair of caps of the present invention, as an option, can come already mated onto the blood ports, and can be removed from the blood ports and used on the dialysate port during priming of the device in order to reduce the risk of caps falling on the floor. Again, this can avoid the cost of creating two different designs of caps per dialyzer package, thus saving production costs per dialyzer package.

With a cap of the present invention, a dialysate port also can be sealed on multiple surfaces (internal and external) using a cap of the present invention. If any polymer residues remain on the interior surface of a dialysate port due to processing techniques, the cap of the present invention can form a fluid-tight seal that seals off such a surface from fluid passing through the port. The capability for the cap of the present invention to seal on the dialysate side (and not requiring a twisting motion) can allow for easier integration with possible future industry requirements to also have the dialysate side of the dialyzer be sterile as presently required for the blood side of the dialyzer.

The cap can be provided with a rounded external design shape combined with relatively softer pliable polymeric material of a controlled hardness, which can also allow for less tearing of overwrap if the caps are placed in the overwrap bags. The closure cap can have a shore A hardness of from about 60 to about 70, or from about 62 to about 68, or about 65, or other hardness values.

Figure 7:
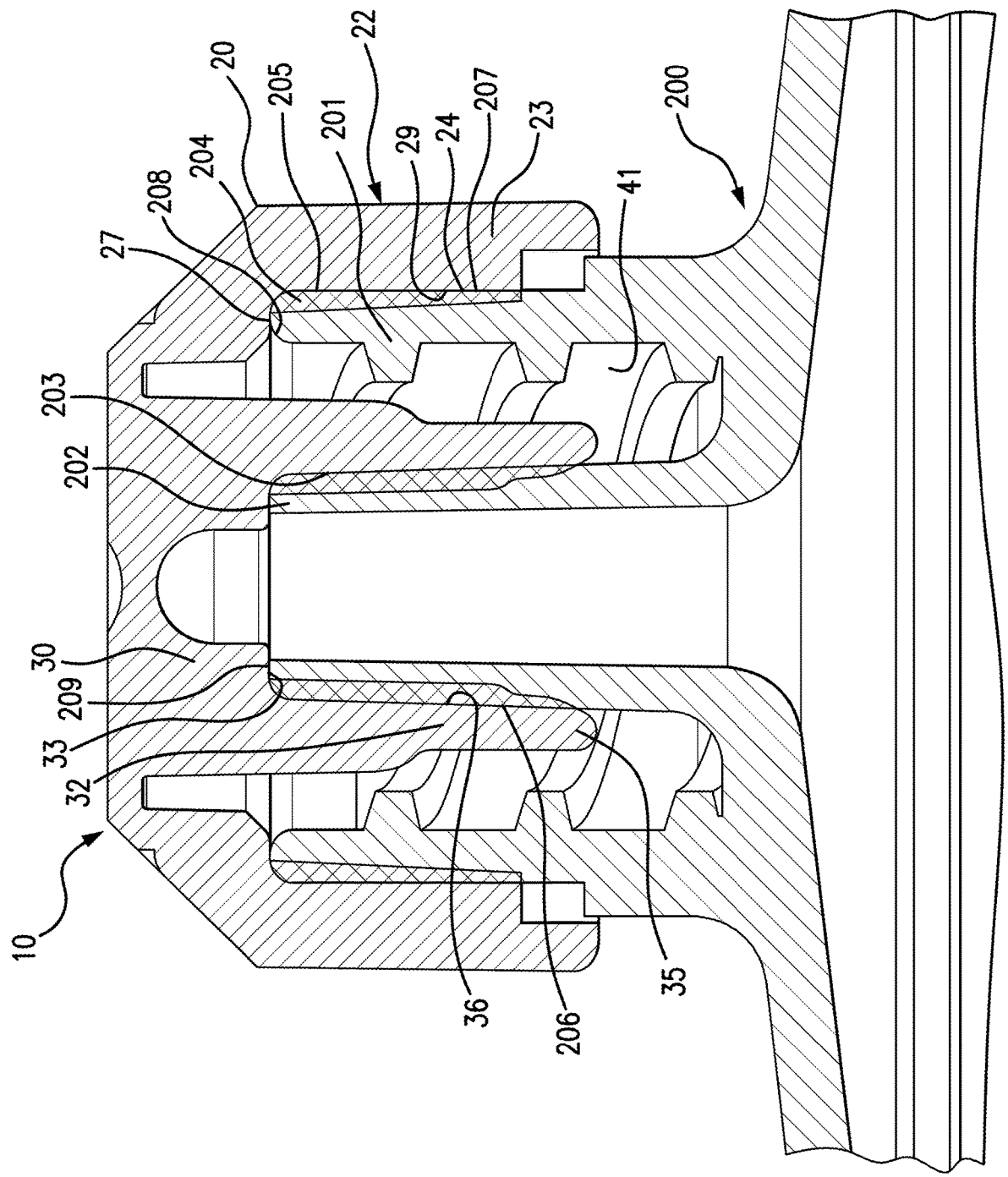
FIG. 7 shows a cross-sectional view of a blood port interface of a closure cap fitted onto a blood port according to an example of the present application.
Figure 8:
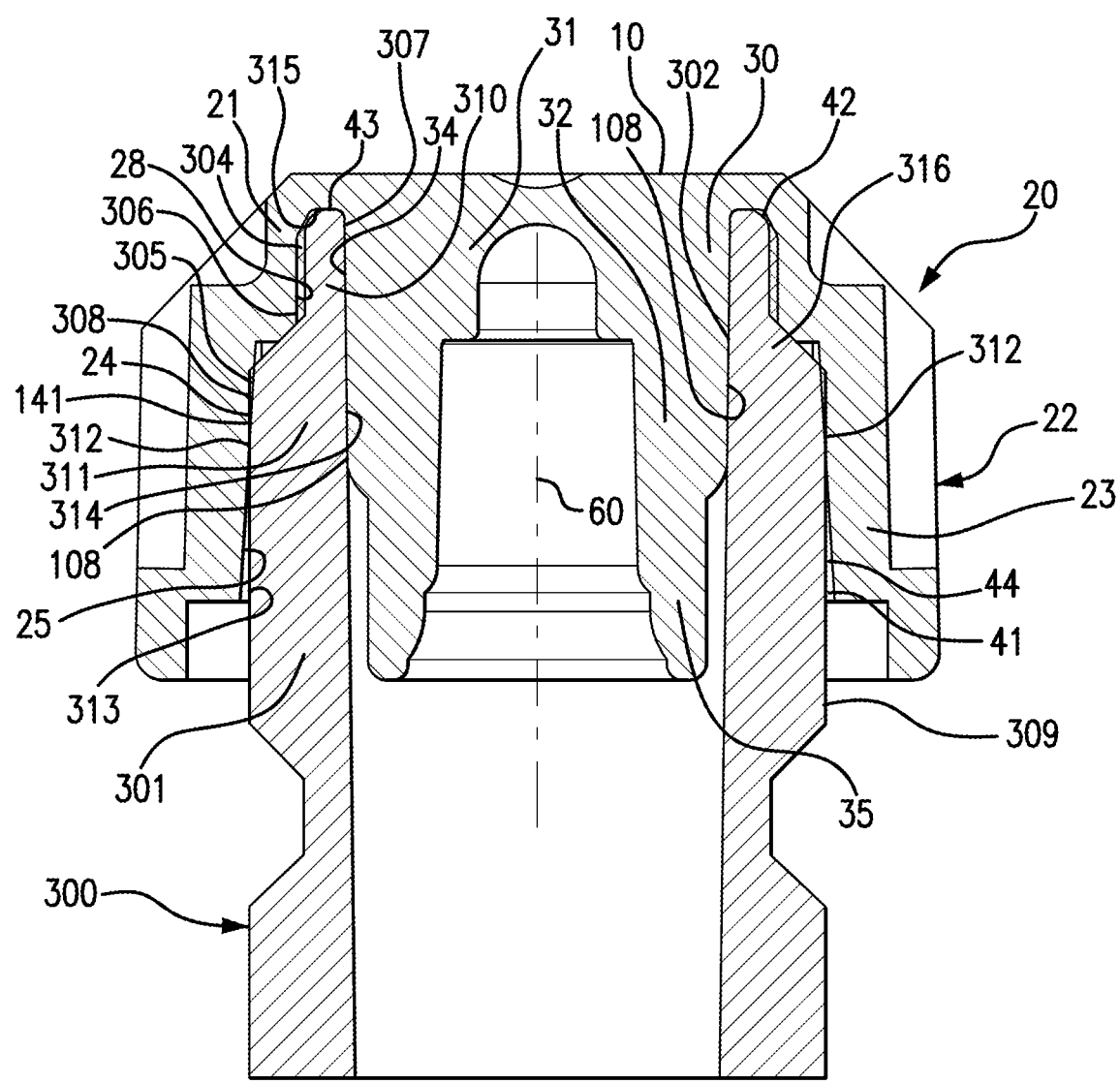
FIG. 8 shows a cross-sectional view of a dialysate port interface of a closure cap fitted onto a dialysate port according to an example of the present application.

With reference to the drawings, FIG. 1 a closure cap 10 is shown for diverse fluid ports on a blood treatment device. The cap 10 has a first skirt 20 and a second skirt 30 located radially within the first skirt 20. The first skirt 20 and the second skirt 30 are separated by an intermediate channel 40. The channel 40 has a lower channel portion 41, and an upper channel portion 42 which has an upper end 43. A transverse connecting portion 50 connects the first skirt 20 and the second skirt 30. The transverse connecting portion 50 comprises an outer exposed surface 51, and the connecting portion 50 extends inward from outer exposed surface 51 a distance to imaginary line 52 (shown by a dashed line), which intersects the upper end 43 of upper channel portion 42. The first skirt 20 comprises a first skirt upper portion 21 and a first skirt lower portion 22. The first skirt upper portion 21 extends away from the transverse connecting portion 50. A circumferential inner side surface 28 of the first skirt upper portion 21 is configured to sealingly engage an upper external surface of a first fluid port on a blood treatment device, such as a dialyzer dialysate port, e.g., as shown in FIG. 8. The first skirt lower portion 22 comprises a cylindrical sleeve portion 23, an inner side surface 25, an outer side surface 45, and a plurality of ribs 24 extending radially inward from the cylindrical sleeve portion 23 towards the lower channel portion 41 of channel 40. The inner side surface 25 and outer side surface 45 of sleeve portion 23 both can be inclined, as an option, at the same small angle α (e.g., 1°-3°) relative to the geometric central axis 60 of the cap 10. The inclined surface plane of the outer side surface 45 can be provided for further ease of grip. The ribs 24 are spaced apart around an inner side surface 25 of the cylindrical sleeve portion 23 with intervening gaps 26. The number of ribs 24 may be from about 4 to about 16, or other numbers. The ribs 24 preferably have the same dimensioned profile shape (e.g., rectangular) and equidistant spacing from each other. The ribs 24 are configured to engage an external shroud surrounding a nipple of a second fluid port on the blood treatment device, such as a DIN blood port, when the cap is press fit onto the blood port, such as shown in FIG. 7. The first skirt 20 has a stop surface 27 for an external shroud surrounding the nipple of a second fluid port on a blood treatment device, such as a DIN blood port.

The second skirt 30 comprises a second skirt upper portion 31 and a second skirt lower portion 32. The second skirt upper portion 31 extends away from the transverse connecting portion 50 and comprises an exposed bottom stop surface 33, and a circumferential external side surface 34 that is surrounded by the upper channel portion 42 of channel 40. The circumferential external side surface 34 of the second skirt upper portion 31 is configured to sealingly engage with an upper internal surface of the first fluid port, such as shown in FIG. 8. The second skirt lower portion 32 comprises a tubular skirt 35 which extends away from the second skirt upper portion 31. As shown in FIG. 1, the second skirt upper portion 31 has a recess 38 at its lower side that opens into a receptacle 37 defined by the tubular skirt 35 of the second skirt lower portion 32. The tubular skirt 35 is externally surrounded by the channel 40 and comprises a circumferential internal side surface 36 that defines a receptacle 37. The closure cap 10 can have a geometric central axis 60 wherein the first skirt lower portion 22 and the tubular skirt 35 can be concentrically arranged with respect to the geometric central axis 60. The circumferential internal side surface 36 of tubular skirt 35 is configured to sealingly engage with an external surface of a second fluid port, such as a blood port, which has a smaller external diameter from that of the first fluid port, such as shown in FIG. 7. The receptacle 37 extends into the cap 10 to the second skirt stop surface 33, which prevents any further insertion of a second port, e.g., a blood port nipple, into the cap 10. The exposed bottom stop surface 33 of the second skirt upper portion 31 can provide a hard stop to pushing of the tubular skirt 35 onto the second fluid port of the blood treatment device. The stop surface 33 can be a physical feedback to let users know that the cap 10 has been successfully applied to the second port, e.g., a blood port nipple. The tubular skirt 35 can be a visual feedback to let users know that the cap 10 has been successfully applied onto the second port.

Figure 2:
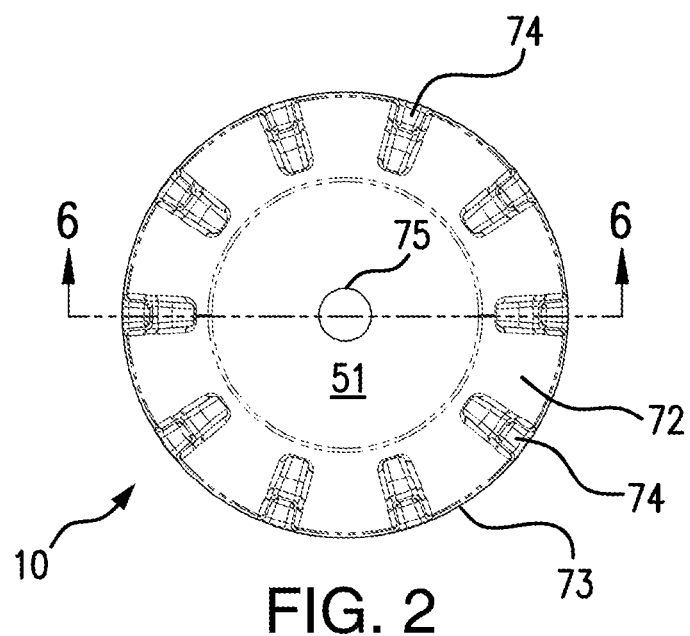
FIG. 2 shows a top plan view of the closure cap of FIG. 1 according to an example of the present application.
Figure 3:
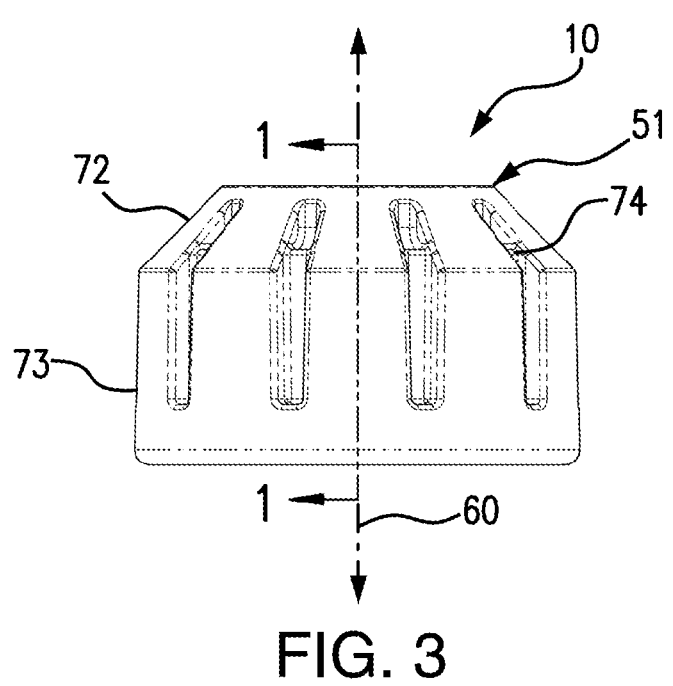
FIG. 3 shows an elevational side view of the closure cap of FIG. 1 according to an example of the present application.

As shown in FIGS. 2 and 3, the closure cap 10 can have essentially a rounded grippable external profile comprised of an upper chamfered edge portion 72, which is the circumferential outer side surface of the first skirt upper portion 21 and the transverse connecting portion 50 shown in FIG. 1. The chamfered portion 72 is located between the generally flat exposed surface 51 and a circumferential lower side surface 73, which is the outside surface of the first skirt lower portion 22 shown in FIG. 1. The chamfer angle for edge portion 72 may be from about 40° to about 50°, e.g., about 45°, or other angles, relative to the geometric central axis 60 of the cap. As an option, the cap 10 also can include partial surface indentations or grooves 74 spaced apart around the circumference of the chamfered portion 72 and lower side surface 73 to facilitate gripping thereof. The slight indentation 75 shown in exposed surface 51 of cap 10 in FIG. 2 is merely an artifact of injection molding the part, and is not a structural feature relevant to the performance of the cap.

Figure 4:
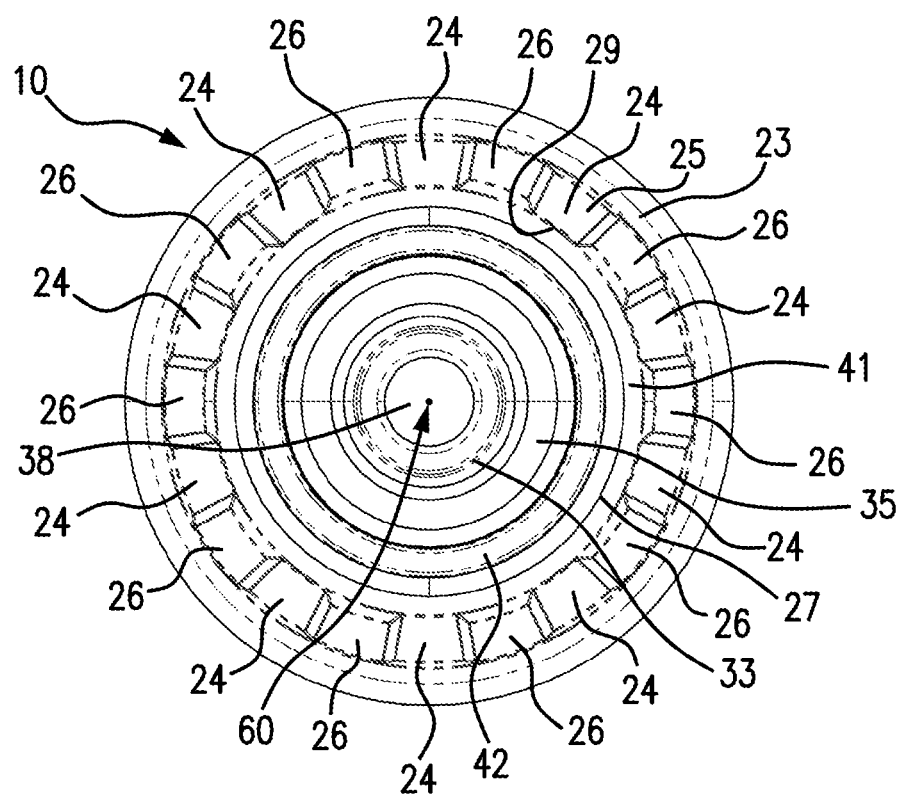
FIG. 4 shows a bottom plan view of the closure cap of FIG. 1 according to an example of the present application.

As shown in more detail in FIG. 4, the ribs 24 are spaced apart around the inner side surface 25 of the cylindrical sleeve portion 23 with intervening gaps 26 between the ribs 24. The ribs 24 can be equidistantly or non-equidistantly spaced apart. The ribs 24 can have the same or substantially the same dimensions (e.g., thicknesses and widths), and similarly the gaps 26 can have the same or substantially the same dimensions (e.g., depths and widths). The ribs 24 optionally may have different width dimensions with respect to each other, and the intervening gaps also would have different widths with respect to each other in that case. The ribs 24 each extend radially inward away from the inner side surface 25 of the cylindrical sleeve portion 23 and towards the geometric central axis 60 of the cap 10. Since the thicknesses of the ribs 24 (measured radially towards the geometric central axis 60) will determine whether the ribs can come into contact with dialysate ports or a blood port shroud inserted into the cap, the ribs 24 preferably have similar thicknesses. The ribs 24 each have an inner facing surface 29, which faces the lower channel portion 41, and which can engage and guide an outer surface of a blood port shroud when the cap is fitted onto a DIN blood port or other blood port having a shroud. Each of the inner facing surfaces 29 of the ribs can be a flat smooth surface. The first skirt stop surface 27, upper channel portion 42, tubular skirt 35, second skirt stop surface 33, and the recess 38 referenced for FIG. 1 are also indicated in FIG. 4.

Figure 5:
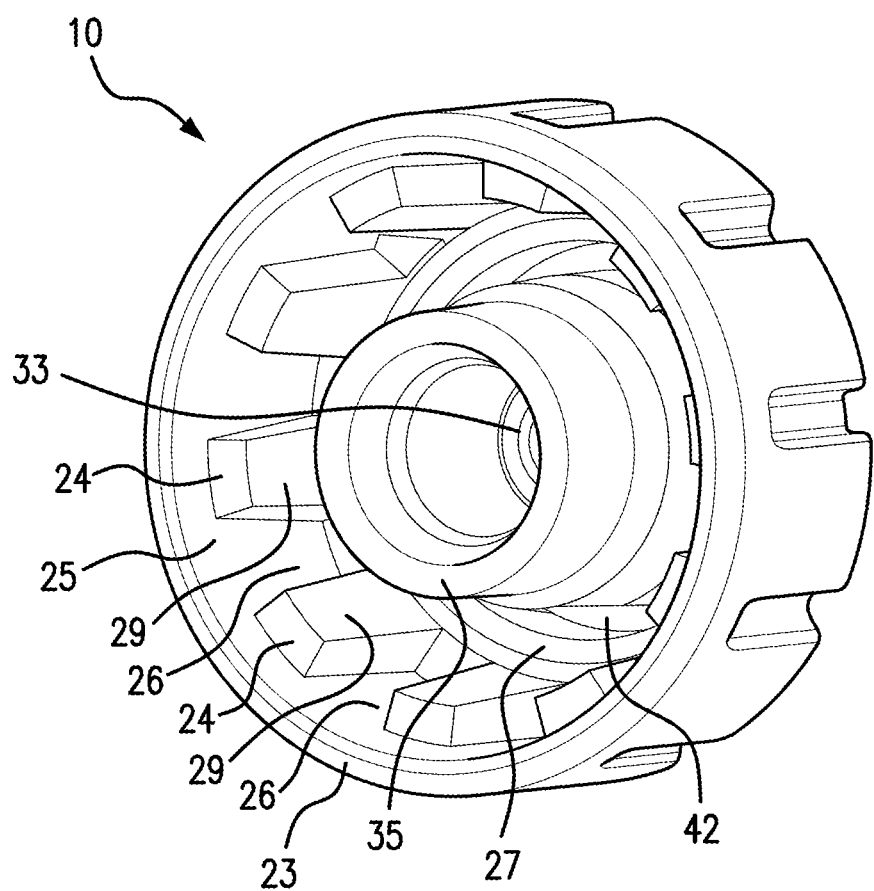
FIG. 5 shows a bottom perspective view of the closure cap of FIG. 1 according to an example of the present application.

As shown in FIG. 5, the ribs 24 of the cylindrical sleeve 23 of the cap 10 which have the inner facing surfaces 29, and the gaps 26 between the inner facing surfaces 29 of adjacent ribs 24, are arranged in an alternating sequence around the inner side surface 25 of the cylindrical sleeve portion 23. The first skirt stop surface 27, upper channel portion 42, the tubular skirt 35, and the second skirt stop surface 33 are also shown in FIG. 5.

Figure 6:
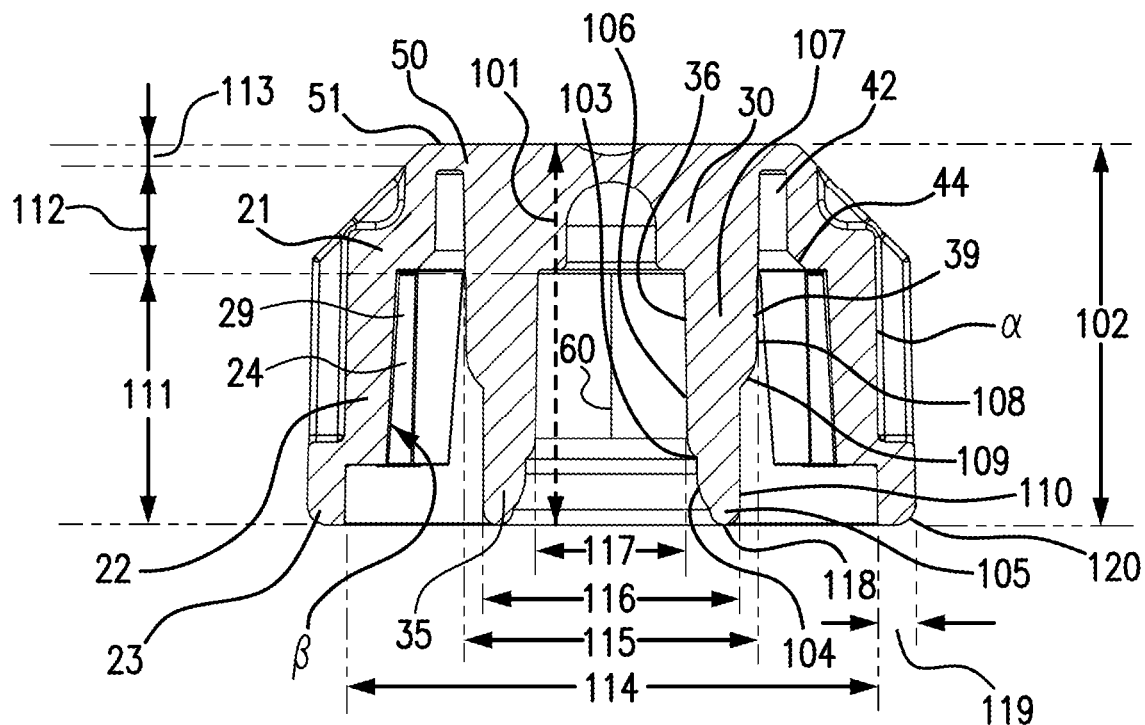
FIG. 6 shows another cross-sectional view of the closure cap according to an example of the present application.

As shown in FIG. 6, the tubular skirt 35 of the second skirt 30 extends in a perpendicular direction away from the outer surface 51 of the transverse connecting portion 50 to a distance 101 which is the same or approximately the same (e.g., within about ±2%) as a distance 102 that the first skirt lower portion 22 extends in a perpendicular direction away from the outer surface 51 of the transverse connecting portion 50. The ribs 24 of the first skirt lower portion 22 extend perpendicularly or substantially perpendicularly (e.g., 90°±5) with respect to the outer surface 51 of the transverse connecting portion 50. The ribs 24, including their inner facing surfaces 29, of the first skirt lower portion 22 can extend at an inclination or draft angle β of 1° to 3° relative to a geometric central axis 60 of the closure cap 10. The circumferential internal side surface 36 of the tubular skirt 35 can have a multi-angled surface contour, which can include rounded surfaces 103 and 104 at the lower distal end 105 of tubular skirt 35 which are contiguous with surface 106 at the upper end 107 which is parallel or substantially parallel (e.g., ±°2) to the geometric central axis 60. The rounded surfaces 103 and 104 sides are present along the internal wall 36 of the tubular skirt 35. The rounded surfaces 103 and 104 can be located where a blood port will seal, and can be used for cap self-alignment when being mated via line-operations. The tubular skirt 35 has a circumferential external side surface 39 which includes an outer surface 108 at its upper end 107 which can be parallel or substantially parallel (e.g., ±°2) to the geometric central axis 60, which can help guide a dialysate port into the upper channel portion 42. The external side surface 39 can include a rounded surface 109 which is contiguous with a lower surface 110 of the surface 39, which also can be parallel or substantially parallel (e.g., ±°2) to the geometric central axis 60. The lower surface 110 can have a rounded surface 118 at its lower distal end. The circumferential sleeve portion 23 can have a non-grooved thickness 119, a lower rounded surface 120, and the inclination angle α. The upper channel portion 42 can have a chamfered portion 44 (e.g., about 45° relative to and away from axis 60).

Normalized to the distance of indicated dimension 101 or 102 of the entire height of the cap 10 as a value of 1.00, the first skirt lower portion 22 can extend a distance 111 of about 0.67, the first skirt upper portion 21 can extend a distance 112 of about 0.27, and the transverse connecting portion 50 can extend a distance 113 of about 0.06. Normalized to the distance of dimension 114 of the greatest inner width of the circumferential sleeve portion 23 as a value of 1.00, the distance 115 between the upper outer surface 108 of the circumferential external side surface 39 of the tubular skirt 35 can be about 0.55, the distance 116 between the lower outer surface 110 of the circumferential external side surface 39 of the tubular skirt 35 can be about 0.48, the distance 117 between rounded surface 103 can be about 0.27, and the nongrooved thickness 119 of the cylindrical sleeve 23 can be 0.08. The radius of curvature (R) of rounded surface 103 can be about 0.035, R of rounded surface 104 can be about 0.08, R of rounded surface 109 can be 0.07, R of rounded surface 118 can be 0.02, and R of rounded surface 120 can be 0.03. As an option, the dimension of the entire height of the cap 101 or 102 can be 0.51 cm, and the distance of dimension 114 can be 0.71 cm.

In FIG. 7, a blood port interface of a closure cap 10 fitted onto a blood port 200 is shown. Blood port 200 can be a DIN blood port. The blood port 200 has an internally threaded shroud or collar 201 and a nipple 202 arranged concentrically within the shroud 201. The nipple 202 is a threadless walled cylindrical structure. The cap 10 is press fit on the blood port 200 with pushing of the cylindrical sleeve 23 of the first skirt lower portion 22 of first skirt 20 over the outer side surface 207 of the blood port shroud 201 concurrent with pushing of the tubular skirt 35 of the second skirt lower portion 32 of second skirt 30 over the outer side surface 206 of the blood port nipple 202. The blood port shroud 201 is an internally-threaded walled cylindrical structure. As the cap 10 is pressed onto the blood port 200, the inner facing surfaces 29 of ribs 24 are the part of cylindrical sleeve 23 of the cap 10 which slidingly engage the outer side surface 207 of the blood port shroud 201, and the circumferential internal side surface 36 of tubular skirt 35 is the part of the cap 10 which slidingly engages the outer side surface 206 of the blood port nipple 202. The pushing of the cap 10 onto the blood port nipple 202 can continue until the second skirt stop surface 33 of second skirt 30 is stopped on an upper end 209 of the blood port nipple 202. The first skirt stop surface 27 of first skirt 20 can be stopped at an upper end 208 of shroud 201. As indicated, the second skirt stop surface 33 can be a physical feedback to let users know that the cap 10 has been successfully applied to the blood port 200, and the tubular skirt 35 can be a visual feedback to let users know that the cap 10 has been successfully applied onto the blood port 200. By this press-fitting of the cap 10 on blood port 200, a sealing contact can be provided between the circumferential internal side surface 36 of tubular skirt 35 and the outer side surface 206 of the blood port nipple 202. As used herein, a "sealing contact" refers to a gas tight seal, a fluid tight seal, or both. The cross hatched portion 204 of shroud 201 indicates the oversize part of the ribs 24 which form part of first skirt lower portion 22 of first skirt 20 which are compressed back and displaced at the inner facing surfaces 29 of the ribs 24 by the shroud 201 to form a continuous rectilinear surface engagement of the outer surface 205 of shroud 201 with inner facing surfaces 29 of the ribs 24. As indicated, the inner facing surfaces 29 of ribs 24 can be flat smooth surfaces which have no lugs provided to thread into the internally threaded shroud 201. The cross hatched portion 203 of blood port nipple 202 indicates the oversize part of tubular skirt 35 of second skirt 30 that is compressed back and displaced at its inner surface 36 by the blood port nipple 202 to form a continuous rectilinear surface engagement of the outer side surface 206 of blood port nipple 202 with inner surface 36 of tubular skirt 35.

In FIG. 8, a dialysate port interface of a closure cap 10 fitted onto a dialysate port 300 is shown. Dialysate port 300 can be a DIN dialysate port. The dialysate port 300 has a lumen 301 on which the cap 10 is press fitted. The lumen 301 is a threadless walled cylindrical structure with a flat inner side surface 302 and a multi-angled outer side surface 309. As the cap 10 is pushed onto the dialysate port 300, upper outer surface 108 of the tubular skirt 35 of the second skirt 30 is brought into sliding engagement with the inner side surface 302 of the upper part 310 of lumen 301. Cap 10 continues to be press-fit onto lumen 301 until the channel upper end 43 of the channel upper portion 42 in the first skirt upper portion 21 forming part of first skirt 20 which is stopped at the upper end 315 of lumen 301. The cross hatched portion 304 of the upper part 310 of lumen 301 indicates the oversize part of the first skirt upper portion 21, which is compressed back and displaced at the first skirt upper circumferential inner side surface 28 of the first skirt upper portion 21 by the outer side surface 306 of the upper part 310 of lumen 301. In this manner, a sealing contact can be made between lumen outer side surface 306 and the first skirt upper circumferential inner side surface 28 of the first skirt upper portion 21. The opposite inner side surface 307 of the upper part 310 of lumen 301 engages, and also can form a sealing contact, with the second skirt upper circumferential external side surface 34 of the second skirt upper portion 31 of second skirt 30.

Still referring to FIG. 8, the cross hatched portion 305 of a lower part 311 of lumen 301 indicates the oversize part of the ribs 24, which are compressed back and displaced at the inner facing surfaces 29 of the ribs 24 by the outer side surface 312 of lumen 301 at portion 308 of surface 312. If the cylindrical sleeve 23 of the first skirt lower portion 22 of first skirt 20 is formed with a draft (inclined) angle relative to the geometric central axis 60, such as shown in FIG. 8, the outer side surface 312 of the lower part 311 of the lumen 301 can engage a limited portion 141 of the inner facing surfaces 29 of the ribs 24 which form part of first skirt lower portion 22 of first skirt 20. The limited contact made between the outer side surface 312 of the lower part 311 of lumen 301 and the portion 141 of the inner facing surfaces 29 of ribs 24 in this manner does not need to be sealing contact. Further, since the inner facing surfaces 29 of the ribs 24 extending inward from the inner side surface 25 of the first skirt lower portion 22 can have an inclination or draft angle relative to the geometric central axis 60 of cap 10, a small gap 44 can occur between a lower portion 313 of the outer side surface 312 of lumen 301 and a portion of the inner facing surfaces 29 of the ribs 24. The opposite inner side 314 of the lower part 311 of lumen 301 contacts the upper outer surface 108 of the tubular skirt 35 of the second skirt lower portion 32 of the second skirt which form a continuous rectilinear surface engagement between those contacting surfaces. As shown in FIG. 8, the lumen 301 also has a chamfered (transition) part 316 between its narrower upper part 310 and wider lower part 311.

The cap of the present invention can be suitable for medical applications, and can be sterilized. The cap can be a molded polymeric product. The cap can be injection molded out of a pliable polymeric material so that the cap can be able to flex to the specific port that the cap is mated with. The polymeric material can be selected from polyvinyl chloride, polyolefin, polyester, polyamide, polysulfone, polyether imide, polyether sulfone, polyphenylene sulfide, polyether ketone, polyether ether ketone, ABS resin, polystyrene, polybutadiene, polyacrylate, polyacrylonitrile, polyacetal, polycarbonate, polyphenylene ether, ethylene-vinyl acetate copolymer, polyvinyl acetate, liquid crystal polymer, ethylene-tetrafluoroethylene copolymer, aromatic polyester, polyvinyl fluoride, polvinylidene fluoride, polyvinylidene chloride, and blends, copolymers, mixtures and composites thereof. The polymer can be colored or can be a neutral white or clear color (non-pigmented). The caps can be provided in the same or different colors by adding a suitable pigment to the molding resin.

FIG. 9 shows a dialyzer 400 which has port caps 10A and 10B, such as described for cap 10 in the additionally discussed figures herein, applied to one of the blood ports 418A and one of the dialysate ports 410A. The depiction of a cap 10A on only one of the blood ports 418A and another cap 10B on only one of the dialysate ports 410A is merely for illustration, and is not limiting. Each of the caps 10A and 10B can be press-fitted onto any one of the blood ports 418A and 418B and dialysate ports 410A and 410B, and multiple caps can be individually press-fitted on both blood ports 418A and 418B at the same time, or both dialysate ports 410A and 410B at the same time, or four of the caps can be press-fitted on all of the blood ports 418A and 418B and dialysate ports 410A and 410B at the same time. The dialyzer port caps 10A and 10B of the present invention can be an original part of the dialyzer 400 before use, or can be attached to ports of a used dialyzer for disposal, or both. The blood ports 418A and 418B can be DIN blood ports, and the dialysate ports 410A and 410B can be DIN dialysate ports.

Apart from the closure caps 10A and 10B, the dialyzer 400 can have a conventional structure. The dialyzer 400 can include, for example, in addition to dialyzer port caps 10A and 10B or any additional such port caps, a large number of microfibers 404 encased in a housing 402. Housing 402 can be a hollow cylinder that opens at both ends. In other designs, housing 402 may be open only at one end, and microfibers 404 can be looped in a U-shape in housing 402 such that both open ends of each microfiber are located at the one open end of housing 402 which has the blood ports (not shown). In either design, thousands of the hollow semipermeable microfibers 404 carry blood in a pathway through one set of open ends of each microfiber 404, through the interior of each microfiber 404, and exiting out of the other open end of each microfiber 404. When the dialyzer 400 is used in a dialysis treatment and its ports are not closed by caps 10A and 10B or the like, the hollow semipermeable microfibers 404 carry blood in a pathway that enters from one end through a first blood inlet/outlet port 418A to the opposite end and out through a second blood inlet/outlet port 418B so that blood flows through the interior of each microfiber 404 in a first direction. Dialysate inlet/outlet ports 410A and 410B are present on opposite ends of housing 402. When not closed by a cap 10B, a first dialysate inlet/outlet port 410B carries dialysate in a pathway into housing 402, the dialysate flows through housing 402 in a countercurrent direction to the blood flow and in the space between each microfiber 404, and a second dialysate inlet/outlet port 418A carries the dialysate out of housing 402. The material exchange thus takes place across the semipermeable membrane that is the walls of each microfiber 404. Label 414 can be a preprinted information label that can be applied after assembly. The design of the dialyzer 400 can produce a high surface area for material exchange in a relatively low volume device. For example, a dialyzer 400 may have about a 5-10 cm cylindrical diameter and about a 20-30 cm length, or other dimensions. A dialyzer with this geometry can accommodate a bundle of about 12,000-13,000 microfibers 404, or other amounts.

The assembly of dialyzer 400 shown in FIG. 9 with the incorporation or retrofitting of the dialyzer port caps 10A and 10B, or additional such caps, on dialyzer ports, can provided in any convenient manner. For example, the assembly of the dialyzer 400 can begin in a customary way, such as by joining rings 408 into each end of housing 402. Each ring 408 can then be joined to housing 402. Many different joining techniques in this respect may be employed, which are generally known in the field, such as spin (friction) welding, laser welding, ultrasonic welding, high frequency welding, gluing, adhesive bonding, solvent bonding, screwing with threads, snap fitting, or any other suitable plastic joining technique. A plurality of nubs 420 spaced apart on the outer surface of ring 408 can constitute spin welding drive features, for example, to assist in a spin welding process. Next, open-ended housing 402 can be filled with a bundle of microfibers, such as microfibers 404, which extend in the longitudinal direction throughout the length of housing 402 and extending a short distance beyond each end. A conventional potting cap (not shown in FIG. 9) can be temporarily attached to each ring 408 to close off each end of housing 402. Housing 402 then can be positioned in a centrifuge to allow rotation about an axis perpendicular to the central longitudinal axis, wherein the axis of rotation extends through the midpoint of housing 402. A potting compound 416, such as polyurethane or epoxy, then can be injected into dialysate inlet/outlet ports 410 on each end of housing 402 which is spun in a centrifuge, and the fibers are effectively potted in the dialyzer. Alternatively, each end of housing 402 may be separately spin welded and injected in a two-step process. The centrifugal force produced by the rotation in the centrifuge forces potting compound 416 to each end, where it sets and hardens. Housing 402 then can be removed from the centrifuge, and each potting cap is removed from each end to expose the hardened potting compound 416 encasing the ends of each microfiber 404. Potting compound 416 and the encased microfibers 404 at each end are then cut through in a plane perpendicular to the central longitudinal axis of housing 402, and the longitudinal axes of the microfibers, to expose the interior channels of each microfiber. The result is that the ends of each microfiber 404 are open for blood flow through the interior channels of each microfiber extending through housing 402, but the rest of the space surrounding each microfiber at both ends of housing 402 is filled with polyurethane, creating a seal between the blood and dialysate. After the potting and cutting process, a flange cap 406 bearing port 418 can be attached to each ring 408 and spin welded together, permanently adhering it to dialyzer 400. Although not shown, the dialyzer may include an O-ring to assist in the sealing of the blood compartment of a dialyzer.

The assembled dialyzer 400 can be sterilized, at least on the blood side of the device, such as using a sterilization process (such steam, irradiation (e.g., E-beam), or chemicals) used or useful for sterilizing dialyzers of other blood treatment devices. The caps of the present invention can be press-fitted onto at least the blood ports of the sterilized dialyzer or other blood treatment device, preferably at the sterilization process station. The caps can be installed on ports of the dialyzer before sterilization, and can be sterilized along with the dialyzer. A cap 10A or 10B, when connected to blood port 418A or 418B, and/or dialysate port 410A or 410B, can block fluid flow via the capped port. Caps 10A and 10B can be fitted to both blood ports 418A and 418B after assembly and sterilization of the device to maintain a gas tight seal before use.

For a hemodialysis treatment, the caps 10A and 10B are removed from the blood and dialysate ports before commencing a treatment on a patient so that blood and dialysate can flow through the device. During a blood treatment, dialysate can enter the dialyzer 410B to flow through the interior of housing 402 in the space surrounding the microfibers 404 in one direction and exits from port 410A. Blood can flow from an arterial blood line from a patient connected to the first blood inlet/outlet port 418A, entering the exposed ends of each microfiber 404, and flowing through the interior channels through the length of housing 402 in a countercurrent direction, and then out of the other exposed ends of each microfiber 404 and back to the patient through a venous blood line connected to a second blood inlet/outlet port 418B. The blood is thus separated from the dialysate by the semipermeable membranes of the microfiber walls, which allow the transfer of liquids, toxins, and nutrients by solute diffusion and pressure gradients.

The dialyzer 400 can be a single use disposable device, wherein the caps 10A and 10B can be removed from or left off the ports during use of the dialyzer and then press-fitted onto the ports after completion of the treatment for closing the blood ports, dialysate port(s), or both types of ports, to block possible flow of residual fluid out from the dialyzer when uninstalled from a dialysis machine for disposal and related handling. After the completion of a dialysis treatment, the blood lines can be disconnected from the ports 418A and 418B, and the caps 10A and 10B can be readily fitted onto the blood ports 418A and 418B to block them. As an option, similar caps of the present invention also can be fitted to the dialysate ports 410A and 410B. The dialyzer 400 with the (re)connected caps 10A and 10B, or additional like caps, can be conveniently and safely handled for disposal.

The present invention includes the following aspects/embodiments/features in any order and/or in any combination:

1. A closure cap for fluid ports on a blood treatment device, comprising:
   a first skirt,
   a second skirt located radially within the first skirt, wherein the first skirt and the second skirt are separated by an intermediate channel, and a transverse connecting portion which connects the first skirt and the second skirt, which comprises an outer surface, wherein
  the first skirt comprises a first skirt upper portion and a first skirt lower portion, wherein the first skirt upper portion extends away from the transverse connecting portion, and a circumferential inner side surface of the first skirt upper portion is configured to sealingly engage an upper external surface of a first fluid port on a blood treatment device, and the first skirt lower portion comprises a cylindrical sleeve portion and a plurality of ribs extending inward from the cylindrical sleeve portion, wherein the ribs are spaced apart around an inner side surface of the cylindrical sleeve portion and are configured to engage an external shroud surrounding a second fluid port on the blood treatment device;
  the second skirt comprises a second skirt upper portion and a second skirt lower portion, wherein the second skirt upper portion extends away from the transverse connecting portion and comprises an exposed bottom stop surface and a circumferential external side surface that is surrounded by the channel, wherein the circumferential external side surface of the second skirt upper portion is configured to sealingly engage with an upper internal surface of the first fluid port, and the second skirt lower portion comprises a tubular skirt which extends away from the second skirt upper portion, wherein the tubular skirt is externally surrounded by the channel and comprises a circumferential internal side surface configured to sealingly engage with an external surface of the second fluid port, wherein the second fluid port has a smaller external diameter from that of the first fluid port, and wherein the exposed bottom stop surface of the second skirt upper portion provides a hard stop to pushing of the tubular skirt onto the second fluid port of the blood treatment device.
2. The closure cap of any preceding or following embodiment/feature/aspect, wherein the tubular skirt of the second skirt extends in a perpendicular direction away from the outer surface of the transverse connecting portion to a distance which is approximately the same (e.g., within about ±2%) as a distance that the first skirt lower portion extends in a perpendicular direction away from the outer surface of the transverse connecting portion.
3. The closure cap of any preceding or following embodiment/feature/aspect, wherein the first skirt upper portion further comprises an exposed bottom stop surface which provides a hard stop to pushing of the cap onto the external shroud surrounding the second fluid port.
4. The closure cap of any preceding or following embodiment/feature/aspect, wherein the ribs of the first skirt lower portion extend perpendicularly or substantially perpendicularly (e.g., 90°±5) with respect to the outer surface of the transverse connecting portion.
5. The closure cap of any preceding or following embodiment/feature/aspect, wherein the ribs of the first skirt lower portion extend at an inclination or draft angle of 1° to 3° relative to a geometric central axis of the closure cap.
6. The closure cap of any preceding or following embodiment/feature/aspect, wherein the ribs are further configured to engage a lower external surface of the first fluid port.
7. The closure cap of any preceding or following embodiment/feature/aspect, wherein the first skirt lower portion and the tubular skirt are concentrically arranged.
8. The closure cap of any preceding or following embodiment/feature/aspect, wherein the circumferential inner side surface of the first skirt upper portion and the circumferential external side surface of the second skirt upper portion are configured to sealingly engage external and inner side surfaces of an ISO-compliant dialysate port.
9. The closure cap of any preceding or following embodiment/feature/aspect, wherein the circumferential inner side surface of the first skirt upper portion and the circumferential external side surface of the second skirt upper portion are configured to sealingly engage external and inner side surfaces of a dialysate port configured according to DIN EN ISO 8637.
10. The closure cap of any preceding or following embodiment/feature/aspect, wherein the circumferential internal side surface of the tubular skirt is configured to sealingly engage an external side surface of an ISO-compliant blood port.
11. The closure cap of any preceding or following embodiment/feature/aspect, wherein the internal side surface of the tubular skirt is configured to sealingly engage an external side surface of a blood port configured according to DIN EN ISO 8637.
12. The closure cap of any preceding or following embodiment/feature/aspect, wherein the tubular skirt is threadless where configured to engage with an external side surface of the second fluid port.
13. The closure cap of any preceding or following embodiment/feature/aspect, wherein the circumferential internal side surface of the tubular skirt has a multi-angled surface contour.
14. The closure cap of any preceding or following embodiment/feature/aspect, wherein the first skirt, the second skirt, and the transverse connecting portion are integrally-formed as a unitary component.
15. The closure cap of any preceding or following embodiment/feature/aspect, wherein the closure cap has a shore A hardness of from about 60 to about 70.
16. The closure cap of any preceding or following embodiment/feature/aspect, wherein the closure cap comprises pliable polymeric material.
17. The closure cap of any preceding or following embodiment/feature/aspect, wherein the closure cap comprises a polymeric material selected from polyvinyl chloride, polyolefin, polyester, polyamide, polysulfone, polyether imide, polyether sulfone, polyphenylene sulfide, polyether ketone, polyether ether ketone, ABS resin, polystyrene, polybutadiene, polyacrylate, polyacrylonitrile, polyacetal, polycarbonate, polyphenylene ether, ethylene-vinyl acetate copolymer, polyvinyl acetate, liquid crystal polymer, ethylene-tetrafluoroethylene copolymer, aromatic polyester, polyvinyl fluoride, polvinylidene fluoride, polyvinylidene chloride, and blends, copolymers, mixtures and composites thereof.
18. A blood treatment device comprising at least one first fluid port having a first external diameter and at least one second fluid port having a second external diameter, wherein the second external diameter is smaller than the first external diameter, and at least one of the at least one first fluid port, the at least one second fluid port, or both, are each closed with a closure cap according to preceding or following embodiment/feature/aspect.
19. The blood treatment device of any preceding or following embodiment/feature/aspect, wherein the blood treatment device is an extracorporeal blood treatment device.

20. The blood treatment device of any preceding or following embodiment/feature/aspect, wherein the blood treatment device is a dialyzer.
21. The dialyzer of any preceding or following embodiment/feature/aspect, wherein the at least one first fluid port comprises first and second dialysate ports and the at least one second fluid port comprises first and second blood ports.
22. The dialyzer of any preceding or following embodiment/feature/aspect, wherein the tubular skirt of the second skirt extends in a perpendicular direction away from the outer surface of the transverse connecting portion to a distance which is approximately the same (e.g., within about ±2%) as a distance that the first skirt lower portion extends in a perpendicular direction away from the outer surface of the transverse connecting portion.
23. The dialyzer of any preceding or following embodiment/feature/aspect, wherein the first skirt upper portion further comprises an exposed bottom stop surface which provides a hard stop to pushing of the cap onto the external shroud surrounding the second fluid port.
24. The dialyzer of any preceding or following embodiment/feature/aspect, wherein the ribs of the first skirt lower portion extend perpendicularly or substantially perpendicularly (e.g., 90°±5) with respect to the outer surface of the transverse connecting portion.
25. The dialyzer of any preceding or following embodiment/feature/aspect, wherein the ribs of the first skirt lower portion extend at an inclination or draft angle of 1° to 3° relative to a geometric central axis of the closure cap.
26. The dialyzer of any preceding or following embodiment/feature/aspect, wherein the ribs are further configured to engage a lower external surface of the first fluid port.
27. The dialyzer of any preceding or following embodiment/feature/aspect, wherein the first skirt lower portion and the tubular skirt are concentrically arranged.
28. The dialyzer of any preceding or following embodiment/feature/aspect, wherein the circumferential inner side surface of the first skirt upper portion and the circumferential external side surface of the second skirt upper portion are configured to sealingly engage external and inner side surfaces of an ISO-compliant dialysate port.
29. The dialyzer of any preceding or following embodiment/feature/aspect, wherein the circumferential inner side surface of the first skirt upper portion and the circumferential external side surface of the second skirt upper portion are configured to sealingly engage external and inner side surfaces of a dialysate port configured according to DIN EN ISO 8637.
30. The dialyzer of any preceding or following embodiment/feature/aspect, wherein the circumferential internal side surface of the tubular skirt is configured to sealingly engage an external side surface of an ISO-compliant blood port.
31. The dialyzer of any preceding or following embodiment/feature/aspect, wherein the internal side surface of the tubular skirt is configured to sealingly engage an external side surface of a blood port configured according to DIN EN ISO 8637.
32. The dialyzer of any preceding or following embodiment/feature/aspect, wherein the tubular skirt is threadless where configured to engage with an external side surface of the second fluid port.
33. The dialyzer of any preceding or following embodiment/feature/aspect, wherein the circumferential internal side surface of the tubular skirt has a multi-angled surface contour.
34. The dialyzer of any preceding or following embodiment/feature/aspect, wherein the first skirt, the second skirt, and the transverse connecting portion are integrally-formed as a unitary component.
35. The dialyzer of any preceding or following embodiment/feature/aspect, wherein the closure cap has a shore A hardness of from about 60 to about 70.
36. The dialyzer of any preceding or following embodiment/feature/aspect, wherein the closure cap comprises pliable polymeric material.
37. The dialyzer of any preceding or following embodiment/feature/aspect, wherein the closure cap comprises a polymeric material selected from polyvinyl chloride, polyolefin, polyester, polyamide, polysulfone, polyether imide, polyether sulfone, polyphenylene sulfide, polyether ketone, polyether ether ketone, ABS resin, polystyrene, polybutadiene, polyacrylate, polyacrylonitrile, polyacetal, polycarbonate, polyphenylene ether, ethylene-vinyl acetate copolymer, polyvinyl acetate, liquid crystal polymer, ethylene-tetrafluoroethylene copolymer, aromatic polyester, polyvinyl fluoride, polvinylidene fluoride, polyvinylidene chloride, and blends, copolymers, mixtures and composites thereof.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the specification and practice of the invention disclosed herein. It is intended that the specification and examples be considered exemplary only, with a true scope and spirit of the invention being indicated by the following claims.

What is claimed is:
1. A closure cap for fluid ports on a blood treatment device, comprising:
a first skirt,
a second skirt located radially within the first skirt, wherein the first skirt and the second skirt are separated by an intermediate channel, and
a transverse connecting portion which connects the first skirt and the second skirt, which comprises an outer surface, wherein
the first skirt comprises a first skirt upper portion and a first skirt lower portion, wherein the first skirt upper portion extends away from the transverse connecting portion, and a circumferential inner side surface of the first skirt upper portion is configured to sealingly engage an upper external surface of a first fluid port on a blood treatment device, and the first skirt lower portion comprises a cylindrical sleeve portion and a plurality of ribs extending inward from the cylindrical sleeve portion, wherein the ribs are spaced apart around an inner side surface of the cylindrical sleeve portion and are configured to engage an external shroud surrounding a second fluid port on the blood treatment device;

the second skirt comprises a second skirt upper portion and a second skirt lower portion, wherein the second skirt upper portion extends away from the transverse connecting portion and comprises an exposed bottom stop surface and a circumferential external side surface that is surrounded by the channel, wherein the circumferential external side surface of the second skirt upper portion is configured to sealingly engage with an upper internal surface of the first fluid port, and the second skirt lower portion comprises a tubular skirt which extends away from the second skirt upper portion, wherein the tubular skirt is externally surrounded by the channel and comprises a circumferential internal side surface configured to sealingly engage with an external surface of the second fluid port, wherein the second fluid port has a smaller external diameter from that of the first fluid port, and wherein the exposed bottom stop surface of the second skirt upper portion provides a hard stop to pushing of the tubular skirt onto the second fluid port of the blood treatment device.

2. The closure cap of claim 1, wherein the tubular skirt of the second skirt extends in a perpendicular direction away from the outer surface of the transverse connecting portion to a distance which is approximately the same as a distance that the first skirt lower portion extends in a perpendicular direction away from the outer surface of the transverse connecting portion.

3. The closure cap of claim 1, wherein the first skirt upper portion further comprises an exposed bottom stop surface which provides a hard stop to pushing of the cap onto the external shroud surrounding the second fluid port.

4. The closure cap of claim 1, wherein the ribs of the first skirt lower portion extend perpendicularly or substantially perpendicularly with respect to the outer surface of the transverse connecting portion.

5. The closure cap of claim 1, wherein the ribs of the first skirt lower portion extend at an inclination angle of 1° to 3° relative to a geometric central axis of the closure cap.

6. The closure cap of claim 1, wherein the ribs are further configured to engage a lower external surface of the first fluid port.

7. The closure cap of claim 1, wherein the first skirt lower portion and the tubular skirt are concentrically arranged.

8. The closure cap of claim 1, wherein the circumferential inner side surface of the first skirt upper portion and the circumferential external side surface of the second skirt upper portion are configured to sealingly engage external and inner side surfaces of an ISO-compliant dialysate port.

9. The closure cap of claim 1, wherein the circumferential inner side surface of the first skirt upper portion and the circumferential external side surface of the second skirt upper portion are configured to sealingly engage external and inner side surfaces of a dialysate port configured according to DIN EN ISO 8637.

10. The closure cap of claim 1, wherein the circumferential internal side surface of the tubular skirt is configured to sealingly engage an external side surface of an ISO-compliant blood port.

11. The closure cap of claim 1, wherein the internal side surface of the tubular skirt is configured to sealingly engage an external side surface of a blood port configured according to DIN EN ISO 8637.

12. The closure cap of claim 1, wherein the tubular skirt is threadless where configured to engage with an external side surface of the second fluid port.

13. The closure cap of claim 1, wherein the circumferential internal side surface of the tubular skirt has a multi-angled surface contour.

14. The closure cap of claim 1, wherein the first skirt, the second skirt, and the transverse connecting portion are integrally-formed as a unitary component.

15. The closure cap of claim 1, wherein the closure cap has a shore A hardness of from 60 to 70.

16. The closure cap of claim 1, wherein the closure cap comprises pliable polymeric material.

17. The closure cap of claim 1, wherein the closure cap comprises a polymeric material selected from polyvinyl chloride, polyolefin, polyester, polyamide, polysulfone, polyether imide, polyether sulfone, polyphenylene sulfide, polyether ketone, polyether ether ketone, ABS resin, polystyrene, polybutadiene, polyacrylate, polyacrylonitrile, polyacetal, polycarbonate, polyphenylene ether, ethylene-vinyl acetate copolymer, polyvinyl acetate, liquid crystal polymer, ethylene-tetrafluoroethylene copolymer, aromatic polyester, polyvinyl fluoride, polvinylidene fluoride, polyvinylidene chloride, and blends, copolymers, mixtures and composites thereof.

18. A blood treatment device comprising at least one first fluid port having a first external diameter and at least one second fluid port having a second external diameter, wherein the second external diameter is smaller than the first external diameter, and at least one of the at least one first fluid port, the at least one second fluid port, or both, are each closed with a closure cap according to claim 1.

19. The blood treatment device of claim 18, wherein the blood treatment device is an extracorporeal blood treatment device.

20. The blood treatment device of claim 18, wherein the blood treatment device is a dialyzer.

21. The blood treatment device of claim 20, wherein the at least one first fluid port comprises first and second dialysate ports and the at least one second fluid port comprises first and second blood ports.

22. The blood treatment device of claim 20, wherein the tubular skirt of the second skirt extends in a perpendicular direction away from the outer surface of the transverse connecting portion to a distance which is ±2% a distance that the first skirt lower portion extends in a perpendicular direction away from the outer surface of the transverse connecting portion.

23. The blood treatment device of claim 20, wherein the first skirt upper portion further comprises an exposed bottom stop surface which provides a hard stop to pushing of the cap onto the external shroud surrounding the second fluid port.

24. The blood treatment device of claim 20, wherein the ribs of the first skirt lower portion extend perpendicularly or substantially perpendicularly with respect to the outer surface of the transverse connecting portion.

25. The blood treatment device of claim 20, wherein the ribs of the first skirt lower portion extend at an inclination angle of 1° to 3° relative to a geometric central axis of the closure cap.

26. The blood treatment device of claim 20, wherein the ribs are further configured to engage a lower external surface of the first fluid port.

27. The blood treatment device of claim 20, wherein the first skirt lower portion and the tubular skirt are concentrically arranged.

28. The blood treatment device of claim 20, wherein the circumferential inner side surface of the first skirt upper portion and the circumferential external side surface of the second skirt upper portion are configured to sealingly engage external and inner side surfaces of an ISO-compliant dialysate port.

29. The blood treatment device of claim 20, wherein the circumferential inner side surface of the first skirt upper portion and the circumferential external side surface of the second skirt upper portion are configured to sealingly engage external and inner side surfaces of a dialysate port configured according to DIN EN ISO 8637.

30. The blood treatment device of claim 20, wherein the circumferential internal side surface of the tubular skirt is configured to sealingly engage an external side surface of an ISO-compliant blood port.

31. The blood treatment device of claim 20, wherein the internal side surface of the tubular skirt is configured to sealingly engage an external side surface of a blood port configured according to DIN EN ISO 8637.

32. The blood treatment device of claim 20, wherein the tubular skirt is threadless where configured to engage with an external side surface of the second fluid port.

33. The blood treatment device of claim 20, wherein the circumferential internal side surface of the tubular skirt has a multi-angled surface contour.

34. The blood treatment device of claim 20, wherein the first skirt, the second skirt, and the transverse connecting portion are integrally-formed as a unitary component.

35. The blood treatment device of claim 20, wherein the closure cap has a shore A hardness of from 60 to 70.

36. The blood treatment device of claim 20, wherein the closure cap comprises pliable polymeric material.

37. The blood treatment device of claim 20, wherein the closure cap comprises a polymeric material selected from polyvinyl chloride, polyolefin, polyester, polyamide, polysulfone, polyether imide, polyether sulfone, polyphenylene sulfide, polyether ketone, polyether ether ketone, ABS resin, polystyrene, polybutadiene, polyacrylate, polyacrylonitrile, polyacetal, polycarbonate, polyphenylene ether, ethylene-vinyl acetate copolymer, polyvinyl acetate, liquid crystal polymer, ethylene-tetrafluoroethylene copolymer, aromatic polyester, polyvinyl fluoride, polvinylidene fluoride, polyvinylidene chloride, and blends, copolymers, mixtures and composites thereof.

* * * * *